United States Patent [19]

Nakai et al.

[11] Patent Number: 5,587,793
[45] Date of Patent: Dec. 24, 1996

[54] BIREFRINGENCE DISTRIBUTION MEASURING METHOD

[75] Inventors: Sadao Nakai, 6-45, Kitakasugaoka 3-chome, Ibaragi-shi, Osaka; Yasukazu Izawa, Suita; Masanobu Yamanaka, Minoo; Masato Ohmi, Toyonaka; Masanori Akatsuka; Chiyoe Yamanaka, both of Osaka; Yoshiyuki Yonezawa, Kawasaki, all of Japan

[73] Assignees: Sadao Nakai; Institute for Laser Technology, both of Osaka; Fuji Electric Co., Ltd., Kanagawa, all of Japan

[21] Appl. No.: 470,157

[22] Filed: Jun. 6, 1995

Related U.S. Application Data

[63] Continuation of Ser. No. 149,811, Nov. 10, 1993, abandoned.

[30] Foreign Application Priority Data

Nov. 12, 1992 [JP] Japan ................... 4-301443

[51] Int. Cl.⁶ ................................ G01N 21/23
[52] U.S. Cl. ................................ 356/367
[58] Field of Search ................... 356/364, 365, 356/366, 367, 368

[56] References Cited

U.S. PATENT DOCUMENTS 5,257,092 10/1993 Noguchi et al. ............ 356/367

FOREIGN PATENT DOCUMENTS 60-29621 2/1985 Japan.

OTHER PUBLICATIONS

"Solid-State Laser Engineering", Koechner, W., Third Completely Revised and Updated Edition, pp. 393–394, 1992.

Masato Noguchi et al., "Measurement of 2-D Birefringence Distribution" SPIE vol. 1720 (1992) pp. 367–378.

V. S. Chudakov, "Investigation of Induced Birefringence with a Rotating Polarization Element" Instrum. & Exper. Techn. vol. 20, (1977) pp. 241–244.

Otani et al., "Two-dimensional Birefringence Measurement Using the Phase Shifting Technique" SPIE vol. 1720, pp. 346–354 (1992).

Matsuura et al, "Measurement of flow-birefringence using a circularly polarized laser beam". *Optics and Laser Technology* vol. 10, No. 5 (Oct. 1978) pp. 237–240.

*Primary Examiner*—Richard A. Rosenberger
*Attorney, Agent, or Firm*—Finnegan, Henderson, Farabow, Garrett & Dunner, L.L.P.

[57] ABSTRACT

A sample is placed between a circular polarizer and an analyzer in an optical path between a monochromatic light source and a two-dimensional optical receiver. Parallel beams emitted from the monochromatic light source are converted into circularly polarized light by the circular polarizer. After transmitting the sample, the light is guided to the analyzer. While rotating the analyzer about the axis of the beams, image data are detected by optical receiver at a step of a regular rotation angle, and the detected image data are sampled to be sent to an image processing device in the next stage. On the basis of the image data, an operation is conducted on each pixel to obtain a relative phase difference due to birefringence of the sample, the two-dimensional birefringence distribution including the sign of the relative phase difference, and also the principal axis direction.

3 Claims, 2 Drawing Sheets

BIREFRINGENCE DISTRIBUTION MEASURING METHOD

This application is a continuation of application Ser. No. 08/149,811 filed Nov. 10, 1993, now abandoned.

BACKGROUND OF THE INVENTION

The invention relates to a birefringence distribution measuring method, and, more particularly, it concerns such a method which obtains quantitatively and two-dimensionally a birefringence distribution induced when thermal or mechanical stress is produced in a laser medium of a solid state laser represented by a YAG laser, for example.

A solid state laser, such as a YAG laser, begins laser oscillation when energy from an excitation light source, such as a lamp, is applied to a laser medium. A part of the lamp light is converted into heat and accumulated in the laser medium so that a temperature gradient or distortion is produced inside the laser medium. As is well known, this causes the laser medium to have optical anisotropy, thereby allowing birefringence to appear.

More particularly, when a temperature gradient is produced inside the laser medium, the difference in thermal expansion between the surface and the center of the medium makes the medium distort, thus generating internal stresses. Similarly, mechanical stresses resulting from mounting the laser medium causes internal stresses in the laser medium. The refractive index of a medium for light depends on stress. As a result, a distribution of refractive indices is produced inside the medium (photoelastic effect).

Also, the refractive index changes in accordance with the polarization direction of light. The refractive index in the direction of the principal axis is different from that of a direction perpendicular to the principal axis, so that when linearly polarized light enters a birefringent substance at an angle to the principal axis of stress produced in the substance, the phase velocities in the two directions are differentiated from each other. The resulting phase difference produces elliptically polarized light. Further, two light beams of different vibration directions progress in different velocities (birefringence) through the birefringent substance. Of the two polarized waves due to birefringence, one wave having one plane of vibration progresses more rapidly, and the other wave progresses slowly. The two waves are called "fast wave" and "slow wave", respectively.

In a solid state laser, a laser beam is amplified when it is reflected back and forth between two mirrors. When birefringence due to the thermal or mechanical stress has occurred inside the laser medium, therefore, the relative phase difference between the two refracted beams causes the wave front to be disturbed, thereby presenting an obstacle to effective laser operation in cases where a laser beam emitted from a laser is output as linearly polarized light and then amplified for use.

From the standpoint of promoting the study of birefringence compensation to obtain a laser beam having a small wave front distortion, therefore, there is a need for an improved method for measuring, two-dimensionally, a birefringence distribution which obtains quantitatively and with high sensitivity birefringence induced in a laser medium of a solid state laser.

Typically, known methods for quantitatively measuring a two-dimensional distribution of birefringence using a conoscope. FIGS. 3 and 4 show in block diagram from systems representing the principle of the known measuring method.

In these figures, 1 designates a sample having a birefringence effect (e.g., a crystal plate or glass plate which is to be used as a laser medium of a solid state laser), 2 designates a monochromatic light source (e.g., He-Ne laser), 3 designates an optical receiver for guiding a received image to a screen, 4 designates a polarizer, 5 designates an analyzer, and 6 and 7 designate quarter-wave plates.

In FIG. 3, the sample 1 is placed between a circular polarizer (a combination of the polarizer 4 and the quarter-wave plate 6) and a circular analyzer (which is a combination of the quarter-wave plate 7 and the analyzer 5 and which is arranged to establish crossed Nicols with respect to the circular polarizer), and arranged in the optical path between the light source 2 and the optical receiver 3. In the configuration, monochromatic parallel beams emitted from the light source 2 are converted into circularly polarized light by the circular polarizer and then projected onto sample 1. The light beams which have undergone birefringence inside the sample 1 pass through the circular analyzer to be detected by the optical receiver 3. When the light intensity after passing through the polarizer 4 is $I_0$, the light intensity detected by the optical receiver 3 is indicated by I, the angle of the axis at a point in the sample 1 which is formed by the vibration direction of the fast wave passing through the sample and the principal plane of the analyzer 5 is indicated by $\phi$, and the relative phase difference between the two beams due to birefringence is indicated by $\delta$, as is well known, the intensity distribution changes in proportion to the equation:

$$I = I_0 \sin^2(\delta/2) \tag{1}$$

In the configuration of FIG. 4 which is the same as that of FIG. 3 except that the quarter-wave plates 6 and 7 are omitted, the intensity distribution changes in proportion to the equation:

$$I = I_0 \sin^2(2\phi) \times \sin^2(\delta/2) \tag{2}$$

In the configuration of FIG. 4, therefore, the intensity distribution of the intensity of the beams passing through the sample 1 and detected by the optical receiver 3 is measured. The direction in which the intensity is zero (I=0) indicates the direction of the principal axis (angle $\phi$). From the intensity to this direction, the relative phase difference 6 can be calculated in accordance with Eq. (2). In the configuration of FIG. 3, the information relating to the direction principal axis is lost, and therefore only the relative phase difference $\delta$ is obtained.

As seen from Eqs. (1) and (2) above, according to the birefringence distribution measuring method using a conoscope, it is possible to obtain the absolute value of the relative phase difference $\delta$ between two refracted beams due to birefringence, and also the two-dimensional distribution of birefringence, but it is impossible to determine the sign of the relative phase difference $\delta$. Further, in Eqs. (1) and (2) above, the relative phase difference $\delta$ is presented in the term of a second degree, $\sin^2(\delta/2)$. Therefore, when the relative phase difference $\delta$ is very small, for example, less than $\pi/4$ radians, the term of $\sin^2(\delta/2)$ is approximated to be $\delta^2/4$, resulting in impaired measurement sensitivity.

As described above, the prior art measuring method cannot judge the sign of the relative phase difference $\delta$. In the state of the art, a simple method of two-dimensionally measuring a birefringence distribution which can obtain both the sign of the relative phase difference and the principal axis direction has not yet been put to practical use.

SUMMARY OF THE INVENTION

The invention has been made in view of the above, and has an objective of providing a novel birefringence distribution measuring method which can measure quantitatively and with high sensitivity a two-dimensional distribution of birefringence induced in a sample, including the sign of the relative phase difference, and obtain the principal axis direction.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

In order to accomplish the objectives, according to the birefringence distribution measuring method of the invention, the sample is placed between a circular polarizer and an analyzer which are in an optical path between a monochromatic light source and a two-dimensional optical receiver; parallel beams emitted from the monochromatic light source are converted into circularly polarized light by the circular polarizer; and the circularly polarized light is passed through the sample and then to the analyzer. The image data are detected by the optical receiver while rotating the analyzer about an axis of the beams, at a step of a fixed rotation angle; the detected image data are sampled and the sampled data are sent to an image processing device. The sampled image data are then processed in the unit of a pixel to obtain a relative phase difference due to birefringence of the sample, a two-dimensional birefringence distribution including the sign of the relative phase difference, and the direction of the principal axis.

When a birefringence distribution of a sample is measured in the above-mentioned arrangement of optical devices or the laser medium is distorted by, for example, irradiating with light (corresponding to the excitation lamp light for a laser) so that the laser medium has optical anisotropy, the intensity, I, of light which has passed through the circular polarizer, the sample, and the circular analyzer is given by the following equation:

$$I=(I_0/2)\times(1\pm\sin 2\phi\times\sin\delta) \quad (3)$$

where $I_0$, $\phi$ and $\delta$ are the same as those used in above equations (1) and (2). In the equation, the symbol ± indicates the rotation direction of circularly polarized light (right-handed direction or left-handed direction). In the case where right-handed circularly polarized light is employed, Eq. (3) above is written as:

$$I=(I_0/2)\times(1+\sin 2\phi\times\sin\delta) \quad (4)$$

When the principal axis direction is inclined in a counterclockwise direction at an angle $\theta$ to the principal plane of the analyzer, the Eq. (4) is written as:

$$I=(I_0/2)\times[1\pm\sin 2(\phi-\theta)\times\sin\delta]tm \quad (5)$$

As seen from Eq. (5), in the state where birefringence has not occurred in the sample, I is equal to $I_0/2$. In contrast, when a birefringence distribution is to be measured in the state where refraction is induced by producing thermal or mechanical stresses in the sample, parallel beams emitted from the monochromatic light source are converted into circularly polarized light by the circular polarizer and then guided through the sample to the analyzer. In this state, the analyzer is rotated by from angle of 0 to 180 degrees about the optical axis, and, for example, seven sets of image data which are detected by the two-dimensional optical receiver at a step of 30 degrees are sampled. The sampled image data are sent to an image processing device in the next stage and stored therein. On the basis of the image data, the image processing device conducts the operation described below on each of the pixels. First, the curve of $\sin 2(\phi-\theta)$ is fitted to each of the pixels of the image data, and, at the position where $\sin 2(\phi-\theta)=1$, the vibration direction (principal axis direction) of the fast wave among the two polarized waves due to birefringence is obtained. Under the conditions at this time, the relative phase difference $\delta$ between the fast wave and the slow wave is calculated from $\sin\delta$ in the above equation, together with the judgment of the sign of the relative phase difference $\delta$. Then, the image processing device conducts these processes on each of the pixels of the image data, whereby both the two-dimensional distribution of birefringence in the sample and the principal axis direction can be measured simultaneously.

As seen from Equations (3) to (5) above, the relative phase difference $\delta$ is presented in a term of the first power, $\sin\delta$. Therefore, when the relative phase difference $\delta$ is very small or less than $\pi/4$ radians the term of $\sin\delta$ is approximated to $\delta$, resulting in that even a minute of relative phase difference $\delta$ can be measured with high sensitivity.

BRIEF DESCRIPTION OF THE DRAWINGS

The accompanying drawings, which are incorporated in and constitute a part of this specification illustrate an exemplary embodiment of the invention and, together with the description, serve to explain the objects, advantages and principles of the invention. In the drawings.

DETAILED DESCRIPTION OF THE PREFERRED EMBODIMENTS

Figure 3:
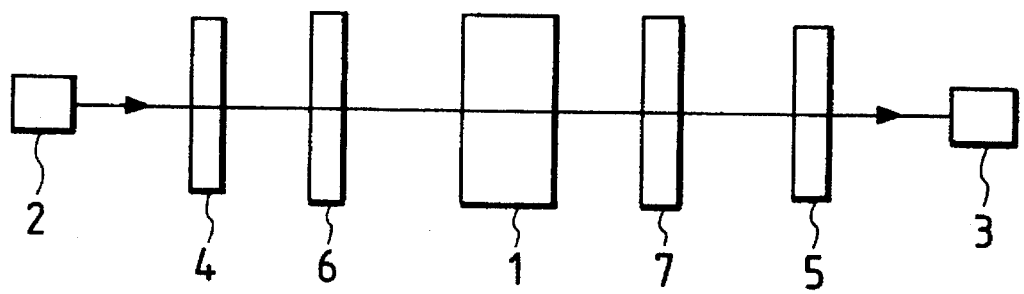
FIG. 3 is a diagram showing the configuration of a prior art birefringence measuring device.
Figure 4:
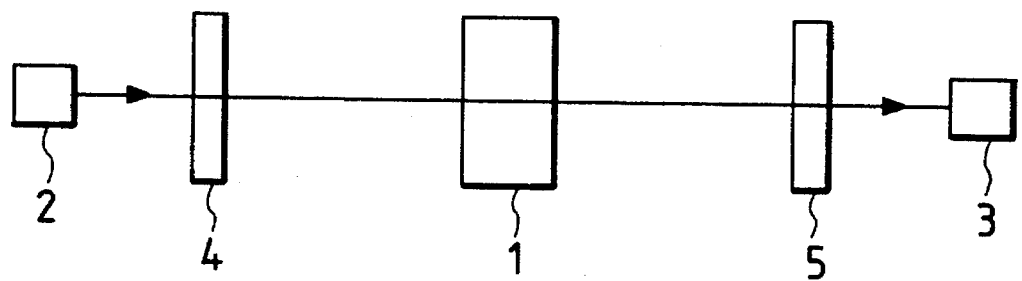
FIG. 4 is a diagram showing the configuration of another prior art birefringence measuring device.

Hereinafter, an embodiment of the invention will be described with reference to FIG. 1. In the figure, components corresponding to those of FIGS. 3 and 4 are designated by the same reference numerals.

Figure 1:
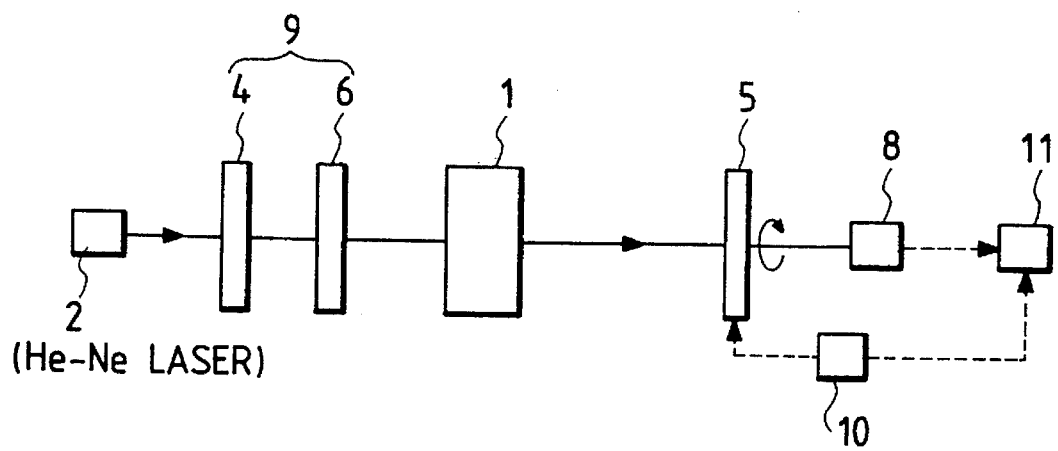
FIG. 1 is a diagram showing the configuration of a two-dimensional birefringence measuring device according to an embodiment of the invention.

In the configuration of FIG. 1, a sample 1 having a birefringence effect is placed between a circular polarizer 9 which is a combination of a polarizer 4 and a quarter-wave plate 6, and an analyzer 5 in an optical path between a monochromatic light source 2 (e.g., He-Ne laser (wavelength: 632.8 nm)) and a two-dimensional optical receiver 8 (e.g., an image pickup device such as a charge coupled device (CCD) camera). The analyzer 5 is provided with a driving mechanism 10 for rotating the analyzer about the optical axis. The two-dimensional optical receiver 8 is connected to an image processing device (computer) 11.

In this configuration, the principal axis of the quarter-wave plate 6 is previously selected, and the rotation direction of circularly polarized light is set to be either the right-handed direction or left-handed direction. During the measurement, monochromatic parallel beams emitted from the light source 2 are converted into circularly polarized light by the circular polarizer 9. After passing through the sample 1, in which birefringence is induced, and the analyzer 5, the light is detected by the two-dimensional optical receiver 8. In the embodiment, the driving mechanism 10 operates so as to rotate the analyzer 5 from an angle of 0 to 180 degrees about the optical axis. In synchronization with the rotation angle, the two-dimensional optical receiver 8 outputs seven sets of image data at a regular angle step of, for example, 30 degrees, and the image data are stored in the image processing device 11. Then, according to Equations (3) to (5) above, the image processing device 11 conducts predetermined operations on each of the pixels of the stored image data, to calculate the relative phase difference $\delta$ at each point of sample 1 in which birefringence is induced, the sign of the relative phase difference, and the principal axis direction, thereby quantitatively obtaining the two-dimensional distribution of birefringence.

Figure 2:
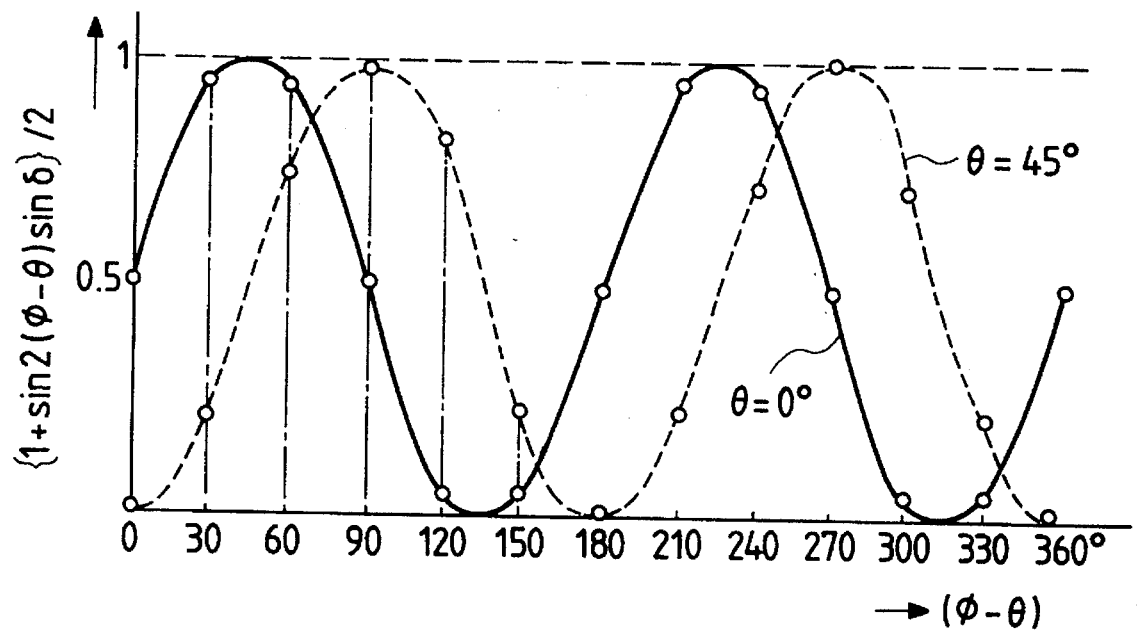
FIG. 2 is a view showing, in the form of a graph a simulation of an example of measuring, a birefringence distribution in accordance with the device of FIG. 1.

FIG. 2 shows, in the form of a graph, a simulation of a measurement example according to the above-described measuring method. In this example, on the assumption that the relative phase difference $\delta$ is $+\pi/2$, the principal axis direction $\theta$ and the relative phase difference $\delta$ are calculated according to Eq. (5) from imaged data obtained in a measurement. In the figure, the solid line indicates the case of $\theta=0$ degrees and the broken line the case of $\theta=45$ degrees. The points at which an image obtained by further rotating the analyzer 5 by 30 degrees about the optical axis is input to the image processing device 11 are indicated on the curves by open circles, respectively.

The computer of the image processing device 11 conducts the curve-fitting so that $(I_0/2)[1+\sin2(\phi-\theta)\times\sin\delta]$ is fitted to each of the open circles, thereby obtaining the curve indicated by the solid line (or the broken line). At the points on the solid line (or broken line) curve where $[1+\sin2(\phi-\theta)\times\sin\delta]/2$ is 1, $\sin\delta$ is +1. From this, it is known that $\delta$ is equal to $+\pi/2$. As a result of the curve-fitting, the principal axis direction is found to be 0 or 45 degrees. This operation is executed on each of the pixels of the image data, so that the two-dimensional distribution of birefringence is obtained.

As described above, according to the birefringence distribution measuring method of the present invention, a two-dimensional distribution due to birefringence, including the sign of the relative phase difference, and also the principal axis direction can be measured quantitatively and with high sensitivity from a sample such as a solid state laser material in which birefringence is induced by thermal or mechanical stress.

The foregoing description of preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A birefringence distribution measuring method of two-dimensionally measuring a birefringence distribution induced in a sample, comprising the steps of:

placing said sample between a circular polarizer and an analyzer in an optical path between a monochromatic light source and a two-dimensional optical receiver;

converting a plurality of parallel beams emitted from said monochromatic light source into circularly polarized light by said circular polarizer;

transmitting said circularly polarized light through said sample to said analyzer;

detecting image data by said two-dimensional optical receiver while rotating said analyzer about an axis of the plurality of beams, at a step of a fixed rotation angle;

sampling said detected image data and sending the sampled data to an image processing device; and processing the sampled image data to obtain a relative phase difference due to birefringence of said sample, a two-dimensional birefringence distribution including the sign of said relative phase difference, and the direction of the principal axis.

2. The method of claim 1, wherein said processing step includes the step of fitting the sampled data to a curve defined by $\sin2(\phi-\theta)$ wherein $\phi$ is the angle of the principal axis and $\theta$ is the angle between the principal axis and the analyzer.

3. The method of claim 2, wherein said processing step further comprises the step of measuring the phase difference due to birefringence at the point where $\sin2(\phi-\theta)=1$.

\* \* \* \* \*

UNITED STATES PATENT AND TRADEMARK OFFICE
CERTIFICATE OF CORRECTION

PATENT NO. : 5,587,793
DATED : December 24, 1996
INVENTOR(S) : Sadao NAKAI et al.

It is certified that error appears in the above-identified patent and that said Letters Patent is hereby corrected as shown below:

Title Page, item [75], Inventors, lines 1-2, "6-45 Kitakasugaoka 3-chome, Ibaragi-shi, Osaka;" should read --Ibaragi;--.

Claim 1, column 6, lines 22-23, "an analyzer" should read --a linear analyzer--.

Claim 1, column 6, line 29, before "analyzer", insert --linear--.

Claim 1, column 6, line 31, before "analyzer", insert --linear--.

Claim 1, column 6, line 37, after "difference", insert --including the sign of said relative phase difference--.

UNITED STATES PATENT AND TRADEMARK OFFICE
CERTIFICATE OF CORRECTION

PATENT NO. : 5,587,793
DATED : December 24, 1996
INVENTOR(S) : Sadao NAKAI et al.

It is certified that error appears in the above-indentified patent and that said Letters Patent is hereby corrected as shown below:

Claim 1, column 6, lines 38-39, after "distribution", delete "including the sign of said relative phase difference".

Signed and Sealed this

Twenty-fourth Day of June, 1997

Attest:

BRUCE LEHMAN

*Attesting Officer*   *Commissioner of Patents and Trademarks*